United States Patent
Nakashima et al.

(10) Patent No.: US 12,186,287 B2
(45) Date of Patent: Jan. 7, 2025

(54) LIDOCAINE-CONTAINING PATCH

(71) Applicant: HISAMITSU PHARMACEUTICAL CO., INC., Tosu (JP)

(72) Inventors: Kentaro Nakashima, Tosu (JP); Yusuke Tanaka, Tosu (JP); Keiichiro Tsurushima, Tosu (JP)

(73) Assignee: HISAMITSU PHARMACEUTICAL CO., INC., Tosu (JP)

(*) Notice: Subject to any disclaimer, the term of this patent is extended or adjusted under 35 U.S.C. 154(b) by 0 days.

(21) Appl. No.: 18/083,793

(22) Filed: Dec. 19, 2022

(65) Prior Publication Data

US 2023/0346720 A1    Nov. 2, 2023

(30) Foreign Application Priority Data

May 2, 2022    (JP) ................. 2022-075744

(51) Int. Cl.
*A61K 31/167*    (2006.01)
*A61K 9/70*    (2006.01)
*A61K 47/10*    (2017.01)

(52) U.S. Cl.
CPC .......... *A61K 31/167* (2013.01); *A61K 9/7046* (2013.01); *A61K 47/10* (2013.01)

(58) Field of Classification Search
CPC ..... A61K 31/167; A61K 9/7046; A61K 47/10
See application file for complete search history.

(56) References Cited

U.S. PATENT DOCUMENTS

| | | |
|---|---|---|
| 2009/0297591 A1 | 12/2009 | Chiang et al. |
| 2010/0280090 A1 | 11/2010 | Hamamoto et al. |
| 2013/0226112 A1 | 8/2013 | Akazawa et al. |
| 2014/0171509 A1 | 6/2014 | Mori et al. |
| 2014/0356412 A1 | 12/2014 | Mori et al. |
| 2015/0174249 A1 | 6/2015 | Hamamoto et al. |
| 2018/0177742 A1 | 6/2018 | Mori et al. |
| 2022/0040121 A1* | 2/2022 | Ogino ............ A61K 47/14 |
| 2022/0354804 A1 | 11/2022 | Inazuki |

FOREIGN PATENT DOCUMENTS

| | | |
|---|---|---|
| CA | 2996485 A1 | 3/2017 |
| CA | 3136186 A1 | 10/2020 |
| CN | 104363900 A | 2/2015 |
| CN | 112438963 A | 3/2021 |
| JP | H10147521 A | 6/1998 |
| JP | 2011521975 A | 7/2011 |
| JP | 2018525419 A | 9/2018 |
| WO | 2009075094 A1 | 6/2009 |
| WO | 2012029325 A1 | 3/2012 |
| WO | 2013046335 A1 | 4/2012 |
| WO | 2012153396 A1 | 11/2012 |
| WO | 2013191187 A1 | 12/2013 |
| WO | 2020250144 A2 | 12/2020 |
| WO | 2020262057 A1 | 12/2020 |

OTHER PUBLICATIONS

CAS RN 137-58-6 (entered STN Nov. 16, 1984) (Year: 1984).*
CAS RN 41340-25-4 (entered STN Nov. 16, 1984) (Year: 1984).*
DailyMed, "Label: Salonpas Pain Relievinglidocaine 4% FLEX—lidocaine patch",https://dailymed.nlm.nih.gov/dailymed/drugInfo.cfm?setid=9507f727-c49f-4de4-9d64-b6d977d568ab, Dec. 22, 2021.
Notice of Allowance dated Apr. 7, 2023 corresponding to TW Patent Application No. 111148879.
Office Action dated Mar. 16, 2023 corresponding to CA Patent Application No. 3185579.

* cited by examiner

*Primary Examiner* — Amy L Clark
*Assistant Examiner* — Chihyi Lee
(74) *Attorney, Agent, or Firm* — Nath, Goldberg & Meyer; Joshua B. Goldberg

(57) ABSTRACT

Disclosed is a patch comprising an adhesive layer on a backing layer, wherein the adhesive layer comprises lidocaine or a pharmaceutically acceptable salt thereof, propylene glycol, a rubber adhesive base and a terpene resin, wherein the content of the lidocaine or a pharmaceutically acceptable salt thereof in the adhesive layer in terms of free form is 2 mass % to 6 mass % with respect to the total mass of the adhesive layer, wherein the ratio of the mass of the lidocaine or a pharmaceutically acceptable salt thereof in terms of free form to the mass of propylene glycol in the adhesive layer is 1:0.6 to 1:1.8, and wherein the content of the terpene resin in the adhesive layer is 5 mass % to 18 mass % with respect to a total mass of the adhesive layer.

2 Claims, No Drawings

LIDOCAINE-CONTAINING PATCH

TECHNICAL FIELD

The present invention relates to a lidocaine-containing patch.

BACKGROUND

Lidocaine, which has a local anesthetic effect, is known to be effective in pain treatment for postoperative pain and neuropathic pain because it provides an analgesic effect when administered at a low dose, and is administered in the form of intramuscular injection, intravenous injection, a drip, gel, a patch and the like. Among these, a transdermal administration method using a patch is a useful administration method because it has advantages such as ease of administration, improved compliance, and sustained effect.

Regarding lidocaine-containing patches, for example, Patent Document 1 (WO 2013/046335) discloses a lidocaine-containing non-aqueous patch using an organic acid, a polyhydric alcohol, or a surfactant as a dissolving agent for keeping lidocaine dissolved. In addition, Patent Document 2 (JP 2018-525419) discloses a non-aqueous patch containing a dissolving agent consisting of a mixture of an organic acid and a polyalcohol.

SUMMARY

The inventors conducted studies regarding a lidocaine-containing patch, and found that, when a polyhydric alcohol is used as a dissolving agent for lidocaine, crystals are precipitated in the patch during production or immediately after production depending on the type of polyhydric alcohol. A patch in which drug crystals are precipitated often have problems that skin permeability of the medicinal substance is lowered and sufficient efficacy cannot be obtained.

In addition, the inventors found that, while a patch comprising a large content of a polyhydric alcohol tends to have low adhesion, adhesive faces tend to strongly adhere to each other and are difficult to separate, i.e., self-adhesion tends to be strong. A patch with strong self-adhesion has problems that, when adhesive faces are accidentally brought into contact with each other, it is difficult to separate them and to apply the patch appropriately.

Therefore, an object of the present invention is to provide a lidocaine-containing patch that suppresses crystal precipitation and suppresses self-adhesion.

The inventors performed extensive studies and found that a patch comprising a certain amount of propylene glycol and a certain amount of a terpene resin in its adhesive layer suppresses crystal precipitation and suppresses self-adhesion, and completed the present invention.

That is, the patch of the present invention has an adhesive layer on a backing layer, the adhesive layer comprises lidocaine or a pharmaceutically acceptable salt thereof, propylene glycol, a rubber adhesive base and a terpene resin, the content of the lidocaine or a pharmaceutically acceptable salt thereof in the adhesive layer in terms of free form is 2 mass % to 6 mass % with respect to the total mass of the adhesive layer, the ratio of the mass of lidocaine or a pharmaceutically acceptable salt thereof in terms of free form to the mass of propylene glycol in the adhesive layer is 1:0.6 to 1:1.8, and the content of the terpene resin in the adhesive is 5 mass % to 18 mass % with respect to the total mass of the adhesive layer.

According to the present invention, it is possible to provide a lidocaine-containing patch that suppresses crystal precipitation, suppresses self-adhesion, and has excellent adhesion.

DETAILED DESCRIPTION

Hereinafter, the present invention will be described in detail with reference to embodiments of the present invention.

A patch according to one embodiment of the present invention has an adhesive layer on a backing layer, the adhesive layer comprises lidocaine or a pharmaceutically acceptable salt thereof, propylene glycol, a rubber adhesive base and a terpene resin, the content of the lidocaine or a pharmaceutically acceptable salt thereof in the adhesive layer in terms of free form is 2 mass % to 6 mass % with respect to the total mass of the adhesive layer, the ratio of the mass of lidocaine or a pharmaceutically acceptable salt thereof in terms of free form to the mass of propylene glycol in the adhesive layer is 1:0.6 to 1:1.8, and the content of the terpene resin in the adhesive layer is 5 mass % to 18 mass % with respect to the total mass of the adhesive layer.

Any backing layer may be used as long as it can maintain the shape of the patch, particularly, the shape of the adhesive layer. Examples of the material of the backing layer include polyamides such as polyethylene, polypropylene, polybutadiene, an ethylene-vinyl chloride copolymer, polyvinyl chloride, and nylon, and synthetic resins such as polyester, a cellulose derivative, and polyurethane. The form of the backing layer is, for example, a film, a sheet, a sheet-like porous component, a sheet-like foaming component, or a fabric such as a woven fabric, a knitted fabric, or a non-woven fabric; or a laminate thereof. The thickness of the backing layer is not particularly limited, and it is usually preferable that the thickness of the backing layer is about 2 μm to 3,000 μm. The basis weight of the backing layer is, for example, 30 $g/m^2$ to 200 $g/m^2$. In this specification, the thickness and the basis weight of the backing layer are measured in accordance with JIS L 1906:2000.

The adhesive layer is formed of an adhesive composition obtained by mixing lidocaine or a pharmaceutically acceptable salt thereof, propylene glycol, a rubber adhesive base, a terpene resin, and an optional component described below. The mass per unit area of the adhesive layer is not particularly limited, and can be 15 $g/m^2$ to 400 $g/m^2$, and may be 50 $g/m^2$ to 300 $g/m^2$, 100 $g/m^2$ to 200 $g/m^2$, or 130 $g/m^2$ to 170 $g/m^2$. When the mass per unit area of the adhesive layer exceeds 400 $g/m^2$, the patch tends to fall off when clothes are put on or taken off. When the mass per unit area of the adhesive layer is less than 15 $g/m^2$, the adhesion of the patch tends to decrease.

The pharmaceutically acceptable salt of lidocaine is a pharmaceutically acceptable acid addition salt of lidocaine. Examples of organic acids include formic acid, acetic acid, adipic acid, citric acid, tartaric acid, methanesulfonic acid, fumaric acid, and maleic acid. Examples of inorganic acids include hydrochloric acid, sulfuric acid, nitric acid, and phosphoric acid. The pharmaceutically acceptable salt of lidocaine is preferably lidocaine hydrochloride. The lidocaine or a pharmaceutically acceptable salt thereof may be an anhydride or a hydrate.

The content of the lidocaine or a pharmaceutically acceptable salt thereof is 2 mass % to 6 mass %, and may be 3 mass % to 5 mass % with respect to a total mass of the adhesive layer. Here, in the case of a patch comprising a pharmaceutically acceptable salt of lidocaine in the adhesive layer, the above mass % is mass % of lidocaine in terms of free form.

Propylene glycol suppresses precipitation of crystals in the patch during production or immediately after production. The ratio of the mass of the lidocaine or a pharmaceutically acceptable salt thereof in terms of free form and the mass of propylene glycol in the adhesive layer is 1:0.6 to 1:1.8, and may be 1:0.75 to 1:1.75. A patch in which the ratio of the mass of lidocaine or a pharmaceutically acceptable salt thereof in terms of free form and the mass of propylene glycol is within the range suppresses crystal precipitation and suppresses self-adhesion. The content of propylene glycol in the adhesive layer can be 1.2 mass % to 7 mass %, and may be 1.8 mass % to 7 mass %, or 3 mass % to 7 mass % with respect to a total mass of the adhesive layer.

The rubber adhesive base imparts adhesiveness to the adhesive layer. Examples of rubber adhesive bases include a styrene-butadiene block copolymer, a styrene-butadiene-styrene block copolymer, a styrene-isoprene block copolymer, a styrene-isoprene-styrene block copolymer, polyisobutylene, natural rubber, an alkyl vinyl ether (co) polymer, polyisoprene, and polybutadiene, and these may be used alone or two or more thereof may be used in combination.

As the rubber adhesive base according to the present embodiment, it is preferable that at least one selected from the group consisting of a styrene-isoprene-styrene block copolymer and polyisobutylene be comprised, and it is more preferable that a styrene-isoprene-styrene block copolymer and polyisobutylene be comprised, in consideration that the preferable adhesive layers tend to exhibit more sufficient adhesion.

Specific examples of styrene-isoprene-styrene block copolymers include QUINTAC® 3570C (product name, commercially available from Zeon Corporation), SIS5002, SIS5229, SIS5505 (product name, commercially available from JSR), and SIBSTAR® T102 (product name, commercially available from Kaneka Corporation). In addition, polyisobutylene also includes so-called butyl rubber (isobutyleneisoprene rubber), and specific examples thereof include OPPANOL® N50, N80, N100, N150, B11, B12, B50, B80, B100, B120, B150, B220 (product name, commercially available from BASF), JSR® Butyl 065, 268, 365 (product name, commercially available from JSR), X-BUTYL® RB100, 101-3, 301, 402 (product name, commercially available from ARLANXEO), and EXXON® Butyl 065, 065S, 068, 068S, 268, 268S, 365, 365S (product name, commercially available from EXXN MOBILE).

The content of the rubber adhesive base can be 10 mass % to 80 mass %, and may be 15 mass % to 60 mass %, or 15 mass % to 40 mass % with respect to a total mass of the adhesive layer.

The adhesive layer can comprise one or more selected from the group consisting of an acrylic adhesive base and a silicone adhesive base in addition to the rubber adhesive base. The total content of the adhesive base can be 10 mass % to 95 mass % or may be 20 mass % to 90 mass % with respect to a total mass of the adhesive layer.

The acrylic adhesive base is, for example, a (co) polymer of one or two or more (meth)acrylic acid alkyl esters. Examples of (meth)acrylic acid alkyl esters include butyl (meth)acrylate, isobutyl (meth)acrylate, hexyl (meth)acrylate, octyl (meth)acrylate, 2-ethylhexyl (meth)acrylate, and decyl (meth)acrylate. Here, in this specification, "(meth) acrylic acid" refers to either or both of acrylic acid and methacrylic acid, and similar expressions are similarly defined.

The acrylic adhesive base may be a copolymer formed from a (meth)acrylic acid alkyl ester (main monomer) and a comonomer. Examples of main monomers include methyl (meth) acrylate, ethyl (meth) acrylate, butyl (meth) acrylate, hexyl (meth) acrylate, heptyl (meth) acrylate, octyl (meth) acrylate, and 2-ethylhexyl (meth) acrylate, and these may be used alone or two or more thereof may be used in combination. The comonomer may be any component as long as it can be copolymerized with (meth)acrylic acid alkyl ester. Examples of comonomers include (meth)acrylic acid hydroxyalkyl ester, ethylene, propylene, styrene, vinyl acetate, N-vinylpyrrolidone, (meth)acrylic acid, and (meth) acrylic acid amide. The comonomers may be used alone or two or more thereof may be used in combination.

Specific examples of acrylic adhesive bases include an acrylic acid/octyl acrylate copolymer, a 2-ethylhexyl acrylate/vinylpyrrolidone copolymer solution, an acrylic acid ester/vinyl acetate copolymer, a 2-ethylhexyl acrylate/2-ethylhexyl methacrylate/dodecyl methacrylate copolymer, a methyl acrylate/2-ethylhexyl acrylate copolymer resin emulsion, and an acrylic polymer contained in an acrylic resin alkanolamine liquid. Specific examples of such acrylic adhesive bases include DURO-TAK® series (commercially available from Henkel) such as DURO-TAK® 387-2510, DURO-TAK® 87-2510, DURO-TAK® 387-2287, DURO-TAK® 87-2287, DURO-TAK® 87-4287, DURO-TAK® 387-2516, DURO-TAK® 87-2516, DURO-TAK® 87-2074, DURO-TAK® 87-900A, DURO-TAK® 87-901A, DURO-TAK® 87-9301, and DURO-TAK® 87-4098; GELVA® series (commercially available from Henkel) such as GELVA® GMS 788, GELVA® GMS 3083, and GELVA® GMS 3253; MAS® series (commercially available from CosMED Pharmaceutical Co., Ltd.) such as MAS®811 (product name) and MAS®683 (product name); and Eudragit® series (commercially available from Evonik Industries), Nikasol® series (commercially available from Nippon Carbide Industries Co., Inc.), and UltraSol® series (commercially available from Aica Kogyo Co., Ltd.).

The content of the acrylic adhesive base can be 10 mass % to 50 mass % or may be 10 mass % to 20 mass % with respect to a total mass of the adhesive layer.

The silicone adhesive base is a compound having an organopolysiloxane framework. Examples of silicone adhesive bases include dimethylpolysiloxane, polymethylvinylsiloxane, and polymethylphenylsiloxane. Specific examples of siliconeadhesive bases include MD series (commercially available from DuPont Toray Specialty Materials K.K.) such as MDR7-4502 Silicone Adhesive and MDR7-4602 Silicone Adhesive; BIO-PSA® series (commercially available from DuPont Toray Specialty Materials K.K.) such as BIO-PSA® 7-4301 Silicone Adhesive, BIO-PSA® 7-4302 Silicone Adhesive, BIO-PSA® 7-4201 Silicone Adhesive, BIO-PSA® 7-4202 Silicone Adhesive, BIO-PSA® 7-4101 Silicone Adhesive, BIO-PSA® 7-4102 Silicone Adhesive, BIO-PSA® 7-4601 Silicone Adhesive, BIO-PSA® 7-4602 Silicone Adhesive, BIO-PSA® 7-4501 Silicone Adhesive, BIO-PSA® 7-4502 Silicone Adhesive, BIO-PSA® 7-4401 Silicone Adhesive, and BIO-PSA® 7-4402 Silicone Adhesive, Dow Corning® 7-9800A, Dow Corning® 7-9800B, Dow Corning® 7-9700A, and Dow Corning® 7-9700B.

The content of the silicone adhesive base can be 10 mass % to 50 mass % and may be 10 mass % to 20 mass % with respect to a total mass of the adhesive layer.

The terpene resin functions as a tackifying resin. The content of the terpene resin is 5 mass % to 18 mass %, and may be 9 mass % to 14 mass % with respect to a total mass of the adhesive layer. A patch comprising a terpene resin within the above content range exhibits sufficient adhesion, and exhibits suppressed self-adhesion.

Examples of terpene resins include a pinene polymer (α-pinene polymer, β-pinene polymer, etc.), a terpene polymer, a dipentene polymer, a terpene-phenol polymer, an aromatic modified terpene polymer, and a pinene-phenol copolymer, and more specifically, YS® resin (YS® resin PXN (1150N, 300N), YS® resin PX1000, YS® resin TO125, YS® resin TO105, etc.), CLEARON® P105, CLEARON® M115, CLEARON® K100 (product name, all are commercially available from Yasuhara Chemical Co., Ltd.), and TAMANOL® 901 (product name, commercially available from Arakawa Chemical Industries, Ltd.) may be exemplified.

The adhesive layer may optionally further comprise other additives. Examples of other additives include a tackifying resin other than a terpene resin, a plasticizer, an absorption enhancer, a dissolving agent other than propylene glycol, a stabilizer, a filler, and a fragrance.

The tackifying resin is a component that adjusts adhesiveness of the adhesive layer. The adhesive layer may comprise a tackifying resin, for example, a petroleum resin, a rosin resin, a phenol resin and a xylene resin, in addition to the terpene resin. Examples of petroleum resins include an alicyclic petroleum resin (alicyclic saturated hydrocarbon resin, etc.), an aliphatic petroleum resin (aliphatic hydrocarbon resin, etc.), and an aromatic petroleum resin, and more specifically, ARKON®P-70, ARKON® P-85, ARKON® P-90, ARKON® P-100, ARKON®P-115, ARKON® P-125, ARKON® M-70, ARKON® M-85, ARKON® M-90, ARKON® M-100, ARKON® M-115, and ARKON® M-125 (product name, commercially available from Arakawa Chemical Industries, Ltd.), and ESCOREZ® 8000 (product name, commercially available from Esso Petroleum Co., Ltd.) may be exemplified. Examples of rosin resins include hydrogenated rosin glycerin ester, ultra-light-colored rosin, ultra-light-colored rosin ester, and acid-modified ultra-light-colored rosin, and more specifically, PINECRYSTAL® (KE-311, PE-590, KE-359, KE-100, etc.) (product name, commercially available from Arakawa Chemical Industries, Ltd.) may be exemplified. In addition to the terpene resin, the tackifying resins may be used alone or two or more thereof may be used in combination. When the adhesive layer comprises a tackifying resin other than the terpene resin, the content of the tackifying resin (the content except for the terpene resin) can be 5 mass % to 50 mass % and may be 10 mass % to 40 mass % with respect to a total mass of the adhesive layer.

Examples of plasticizers include liquid paraffin, light liquid paraffin, squalane, squalene, a vegetable oil (olive oil, *camellia* oil, castor oil, tall oil, peanut oil, spearmint oil, *eucalyptus* oil, jojoba oil, camphor white oil, sunflower oil, orange oil, etc.), fats and oils (dibutyl phthalate, dioctyl phthalate, etc.), and liquid rubber (liquid polybutene, liquid isoprene rubber, etc.). These plasticizers may be used alone or two or more thereof may be used in combination. When the adhesive layer comprises a plasticizer, the content thereof is, for example, 3 mass % to 50 mass %, 10 mass % to 50 mass %, or 20 mass % to 50 mass % with respect to a total mass of the adhesive layer.

The absorption enhancer may be any compound that is conventionally known to have a transdermal absorption enhancing function. Examples of absorption enhancers include an organic acid ester (for example, fatty acid ester, cinnamic acid ester), an organic acid amide (for example, fatty acid amide), a fatty alcohol, a polyhydric alcohol, and an ether (for example, aliphatic ether, polyoxyethylene alkyl ether). These absorption enhancers may have an unsaturated bond and may have a cyclic, linear or branched chemical structure. In addition, the absorption enhancer may be a monoterpene compound, a sesquiterpene compound or a vegetable oil (for example, olive oil). These absorption enhancers may be used alone or two or more thereof may be used in combination.

Examples of the organic acid esters include ethyl acetate, propyl acetate, cetyl lactate, lauryl lactate, methyl salicylate, ethylene glycol salicylate, methyl cinnamate, and a fatty acid ester. Examples of fatty acid esters include methyl laurate, hexyl laurate, isopropyl myristate, myristyl myristate, octyldodecyl myristate, isopropyl palmitate, and cetyl palmitate. The fatty acid ester may be a glycerin fatty acid ester, a propylene glycol fatty acid ester, a sorbitan fatty acid ester, a polyethylene glycol sorbitan fatty acid ester, a polyethylene glycol fatty acid ester, a sucrose fatty acid ester, or a polyoxyethylene hydrogenated castor oil. Specific examples of fatty acid esters include glycerin monocaprylate, glycerin monocaprate, glycerin monolaurate, glycerin monooleate, sorbitan monolaurate, sucrose monolaurate, polysorbate 20, propylene glycol monolaurate, polyethylene glycol monolaurate, polyethylene glycol monostearate, Span®40, SPAN®60, SPAN®80, SPAN®120 (product name, commercially available from Croda Japan), TWEEN® 20, TWEEN® 21, TWEEN® 40, TWEEN® 60, TWEEN® 80, and NIKKOL® HCO-60 (product name, commercially available from Nikko Chemicals Co., Ltd.).

Examples of the organic acid amides include a fatty acid amide (for example, lauric acid diethanolamide), hexahydro-1-dodecyl-2H-azepin-2-one (also referred to as Azone) and a derivative thereof, and pyrothiodecane.

The fatty alcohol is a fatty alcohol having 6 to 20 carbon atoms. Examples of the fatty alcohols include lauryl alcohol, myristyl alcohol, oleyl alcohol, isostearyl alcohol, and cetyl alcohol.

The aliphatic ether is an ether having an aliphatic group having 6 to 20 carbon atoms (for example, an alkyl group and an alkenyl group). Examples of the polyoxyethylene alkyl ethers include polyoxyethylene lauryl ether.

Examples of the monoterpene compounds include geraniol, thymol, terpineol, 1-menthol, borneol, d-limonene, isoborneol, nerol and dl-camphor. As the monoterpene compound, a peppermint oil may be used.

When the adhesive layer comprises an absorption enhancer, the content of the absorption enhancer can be 0.5 mass % to 20 mass % with respect to a total mass of the adhesive layer.

The dissolving agent is a component that facilitates dissolution of lidocaine or a pharmaceutically acceptable salt thereof in the adhesive composition. The adhesive layer may also comprise a dissolving agent, for example, a fatty acid polyhydric alcohol ester (for example, propylene glycol monolaurate, glyceryl monolaurate, glyceryl monooleate, sorbitan monolaurate), a fatty acid amide (for example, lauric acid diethanolamide), a fatty alcohol (for example, octyldodecanol, isostearyl alcohol, oleyl alcohol), a polyhydric alcohol (for example, dipropylene glycol, polyethylene glycol), and a pyrrolidone derivative (for example, N-methyl-2-pyrrolidone), in addition to propylene glycol. In addition to propylene glycol, these dissolving agents may be used alone or two or more thereof may be used in combination. When the adhesive layer comprises a dissolving agent other than propylene glycol, the content of the dissolving agent (the content except for propylene glycol) can be 2 mass % to 10 mass % with respect to a total mass of the adhesive layer.

Any stabilizer can be used as long as it can suppress formation of free radicals generated by the effect of light beams such as ultraviolet rays, heat or active chemical species, and progress of chain reactions thereof. Examples of stabilizers include tocopherol and an ester derivative thereof, ascorbic acid and an ester derivative thereof, 2,6-dibutylhydroxytoluene (BHT), butyl hydroxyanisole (BHA), and 2-mercaptobenzimidazole. The stabilizers may be used alone or two or more thereof may be used in combination. When the adhesive layer comprises a stabilizer, the content of the stabilizer can be 0.05 mass % to 3 mass %, and may be 0.05 mass % to 1 mass %, 0.05 mass % to 0.25 mass % or 0.1 mass % to 0.25 mass % with respect to a total mass of the adhesive layer.

Examples of fillers include a powder of metal compounds (aluminum oxide, aluminum hydroxide, zinc oxide, titanium oxide, calcium carbonate, etc.), a ceramic (talc, clay, kaolin, silica, hydroxyapatite, synthetic aluminum silicate, magnesium aluminometasilicate, etc.), or an organic compound (cellulose powder, stearate, etc.); or a short fiber of resins comprising them. The fillers may be used alone or two or more thereof may be used in combination. When the adhesive layer comprises a filler, the content of the filler can be 0.1 mass % to 20 mass % with respect to a total mass of the adhesive layer.

The patch may further comprise a release liner. The release liner is laminated on the surface of the adhesive layer opposite to the backing layer. When a patch comprises a release liner, the patch tends to suppress adhesion of dust and the like to the adhesive layer during storage. The surface of the release liner in contact with the adhesive layer is preferably subjected to a release treatment with silicone, fluorinated polyolefin or the like.

The material of the release liner is not particularly limited, and any liner generally known to those skilled in the art can be utilized. Examples of release liners include paper; polyesters such as polyethylene terephthalate and polyethylene naphthalate; polyolefins such as polyethylene and polypropylene; and polyvinyl chloride, polyvinylidene chloride, nylon, and aluminum films. The release liner may be a film in which woodfree paper and polyolefin are laminated. As the material of the release liner, a polypropylene or polyethylene terephthalate film is preferable.

The patch can be produced by, for example, the following method, but the method is not limited thereto and a known method can be utilized. First, components constituting an adhesive layer are mixed at a certain ratio to obtain a uniform dissolved material (adhesive composition). Next, an adhesive layer is formed by spreading the adhesive composition on a releasable film (release liner) to a certain thickness. In addition, a backing layer is pressed against the adhesive layer so that the adhesive layer is interposed between the release liner and the backing layer. Finally, a patch can be obtained by cutting into a desired shape and size. In this case, the release liner is removed when the patch is applied. The area of the patch may be 5 $cm^2$ to 200 $cm^2$, or 50 $cm^2$ to 150 $cm^2$. The shape and size of the patch may be, for example, a rectangle with a short side of 2 cm to 10 cm and a long side of 3 cm to 15 cm or a circle with a diameter of 1 cm to 8 cm.

EXAMPLES

1. Preparation of Patch

According to Tables 1 to 3, respective components were mixed to obtain an adhesive composition. The obtained adhesive composition was spread on a release liner (a polyethylene terephthalate film subjected to a mold release treatment) so that the mass per unit area was 150 $g/m^2$ to form an adhesive layer. A backing layer (polyethylene terephthalate knitted fabric, thickness: 550 μm, basis weight: 110 $g/m^2$) was laminated on the surface of the obtained adhesive layer opposite to the release liner to obtain a patch in which the backing layer/adhesive layer/release liner were laminated in this order.

2. Evaluation Method

The obtained patches were evaluated in accordance with the following evaluation method.

(a) Crystal Precipitation

No: no crystal precipitation was observed in the patch during production or immediately after production.

Yes: crystal precipitation was observed in the patch during production or immediately after production.

(b) Self-Adhesion

The produced patch was cut into a size of 20 mm×70 mm, the patch was set in a tensile testing machine so that the distance between chucks was 30 mm, and then the adhesive surfaces were then attached to each other by putting the chucks closer to each other with a distance of 5 mm. Then, the patch was pulled at a rate of 50 mm/min, and the average value of three integrated average loads (N) from 0 mm to 25 mm was measured as a force required to release the adhesive surface of each patch. In a patch that required a force of 1.3 N or less to release the adhesive surfaces, they could be easily separated when the adhesive surfaces were adhered to each other.

(c) Adhesion

In accordance with the inclined ball tack test (The Japanese Pharmacopoeia, 18th Edition, General Tests, 6.12 Methods of Adhesion Testing), when a ball of No. 30 (diameter: 15/16 inches) or less was rolled from the upper end of the inclined plate, the maximum ball number at which the ball was stopped was evaluated as the adhesion of each patch. When the maximum ball number stopped by a preparation is large, the preparation has excellent adhesion.

TABLE 1

| | Example 1 | Comparative Example 1 | Comparative Example 2 | Comparative Example 3 |
|---|---|---|---|---|
| | mass % | | | |
| Lidocaine | 4.0 | 4.0 | 4.0 | 4.0 |
| Propylene glycol | 3.0 | — | — | — |
| Polyethylene glycol (PEG400) | — | 4.0 | — | — |
| Polypropylene glycol (polypropylene glycol 2000) | — | — | 4.0 | — |
| Glycerin | — | — | — | 4.0 |
| Terpene resin | 14.0 | 14.0 | 14.0 | 14.0 |
| Styrene-isoprene-styrene block copolymer | 26.5 | 26.5 | 26.5 | 26.5 |
| Polyisobutylene | 11.2 | 11.2 | 11.2 | 11.2 |
| Liquid paraffin | 40.4 | 39.4 | 39.4 | 39.4 |
| Other | 0.9 | 0.9 | 0.9 | 0.9 |
| Sum | 100.0 | 100.0 | 100.0 | 100.0 |
| Crystal precipitation | no | yes | yes | yes |

TABLE 1-continued

| | | mass % | | |
|---|---|---|---|---|
| | Example 1 | Comparative Example 1 | Comparative Example 2 | Comparative Example 3 |
| Self-adhesion: force (N) required to release adhesive surface | 1.18 | — | — | — |
| Adhesion (stopped maximum ball No.) | 30 | 30 | 29 | 30 |

Crystals were not precipitated in the patch comprising propylene glycol as a polyhydric alcohol (Example 1), but crystals were precipitated in the patches comprising polyethylene glycol, polypropylene glycol or glycerin as a polyhydric alcohol (Comparative Examples 1 to 3). Here, the self-adhesion of the patches of Comparative Examples 1 to 3 was not evaluated because crystals were precipitated.

TABLE 2

| | mass % | | | | | |
|---|---|---|---|---|---|---|
| | Comparative Example 4 | Comparative Example 5 | Example 1 | Example 2 | Comparative Example 6 | Comparative Example 7 |
| Lidocaine | 4.0 | 4.0 | 4.0 | 4.0 | 4.0 | 4.0 |
| Propylene glycol | — | 2.0 | 3.0 | 7.0 | 8.0 | 14.0 |
| Terpene resin | 14.0 | 14.0 | 14.0 | 14.0 | 14.0 | 14.0 |
| Styrene-isoprene-styrene block copolymer | 26.5 | 26.5 | 26.5 | 26.5 | 26.5 | 26.5 |
| Polyisobutylene | 11.2 | 11.2 | 11.2 | 11.2 | 11.2 | 11.2 |
| Liquid paraffin | 43.4 | 41.4 | 40.4 | 36.4 | 35.4 | 29.4 |
| Other | 0.9 | 0.9 | 0.9 | 0.9 | 0.9 | 0.9 |
| Sum | 100.0 | 100.0 | 100.0 | 100.0 | 100.0 | 100.0 |
| Lidocaine: propylene glycol | — | 1:0.5 | 1:0.75 | 1:1.75 | 1:2 | 1:3.5 |
| Crystal precipitation | yes | yes | no | no | no | no |
| Self-adhesion: force (N) required to release adhesive surface | 1.03 | 1.13 | 1.18 | 1.30 | 1.36 | 1.26 |
| Adhesion (stopped maximum ball No.) | — | 30 | 30 | 30 | 29 | — |

In the patches in which the mass ratio of lidocaine to propylene glycol was in a range of 1:0.6 to 1:1.8 (Examples 1 and 2), crystals were not precipitated, self-adhesion was suppressed, and adhesion was superior. In the patch without propylene glycol (Comparative Example 4), adhesion was not evaluated because crystals were precipitated. Since the patch of Comparative Example 7 comprised a large amount of propylene glycol, it was not suitable as a preparation because so-called bleeding (exudation of the liquid component to the surface of the adhesive layer) occurred. Therefore, adhesion of the patch of Comparative Example 7 was not evaluated. In the patch in which the mass ratio of lidocaine to propylene glycol was 1:0.5 (Comparative Example 5), crystals were precipitated. The patch in which the mass ratio of lidocaine to propylene glycol was 1:2 (Comparative Example 6) had strong self-adhesion and poor adhesion.

TABLE 3

| | mass % | | | | | | |
|---|---|---|---|---|---|---|---|
| | Example 1 | Comparative Example 8 | Comparative Example 9 | Example 3 | Example 2 | Comparative Example 10 | Comparative Example 11 |
| Lidocaine | 4.0 | 4.0 | 4.0 | 4.0 | 4.0 | 4.0 | 4.0 |
| Propylene glycol | 3.0 | 4.0 | 7.0 | 7.0 | 7.0 | 7.0 | 7.0 |
| Terpene resin | 14.0 | — | 4.0 | 9.0 | 14.0 | 19.0 | 24.0 |
| Hydrogenated rosin glycerin ester | — | 14.0 | — | — | — | — | — |
| Styrene-isoprene-styrene block copolymer | 26.5 | 26.5 | 26.5 | 26.5 | 26.5 | 26.5 | 26.5 |

TABLE 3-continued mass %

| | Example 1 | Comparative Example 8 | Comparative Example 9 | Example 3 | Example 2 | Comparative Example 10 | Comparative Example 11 |
|---|---|---|---|---|---|---|---|
| Polyisobutylene | 11.2 | 11.2 | 11.2 | 11.2 | 11.2 | 11.2 | 11.2 |
| Liquid paraffin | 40.4 | 39.4 | 39.4 | 41.4 | 36.4 | 31.4 | 26.4 |
| Other | 0.9 | 0.9 | 0.9 | 0.9 | 0.9 | 0.9 | 0.9 |
| Sum | 100.0 | 100.0 | 100.0 | 100.0 | 100.0 | 100.0 | 100.0 |
| Lidocaine: propylene glycol | 1:0.75 | 1:1 | 1:1.75 | 1:1.75 | 1:1.75 | 1:1.75 | 1:1.75 |
| Crystal precipitation | no | no | no | no | no | no | no |
| Self-adhesion: force (N) that is required to release adhesive surface | 1.18 | 0.60 | 0.83 | 1.07 | 1.30 | 2.47 | 3.71 |
| Adhesion (stopped maximum ball No.) | 30 | 26 | 29 | 30 | 30 | 30 | 30 |

In the patches in which the content of the terpene resin was 5 mass % to 18 mass % (Examples 1 to 3), crystals were not precipitated, self-adhesion was suppressed, and adhesion was superior. The patch comprising hydrogenated rosin glycerin ester in place of the terpene resin (Comparative Example 8) had very poor adhesion. The patch in which the content of the terpene resin was 4 mass % (Comparative Example 9) had poor adhesion. The patches in which the content of the terpene resin was 19 mass % to 24 mass % (Comparative Examples 10 and 11) had strong self-adhesion.

The invention claimed is:

1. A patch comprising an adhesive layer on a backing layer,
    wherein the adhesive layer comprises lidocaine or a pharmaceutically acceptable salt thereof and propylene glycol, a rubber adhesive base and a terpene resin,
    wherein the content the lidocaine or pharmaceutically acceptable salt thereof in the adhesive layer is 2 mass % to 6 mass % with respect to the total mass of the adhesive layer,
    the content of the terpene resin in the adhesive layer is 5 mass % to 18 mass % with respect to the total mass of the adhesive layer,
    the content of propylene glycol in the adhesive layer is 3 mass % to 7 mass % with respect to the total mass of the adhesive layer,
    and the ratio of the mass of the lidocaine or pharmaceutically acceptable salt thereof to the mass of propylene glycol is 1:0.6 to 1:1.8 in relation to each other in the adhesive layer,
    wherein crystals are not precipitated in the patch, and
    wherein the adhesive layer has an adhesive surface, and requires a force of 1.3 N or less to release the adhesive surfaces during self-adhesion.

2. The patch according to claim 1, wherein the content of the terpene resin in the adhesive layer is 9 mass % to 14 mass % with respect to the total mass of the adhesive layer.

* * * * *